(12) United States Patent
Marshall

(10) Patent No.: US 6,725,481 B1
(45) Date of Patent: Apr. 27, 2004

(54) BODY POSITIONER

(76) Inventor: Mabel E. Marshall, 14650 Sussex Hwy., Bridgeville, DE (US) 19933

( * ) Notice: Subject to any disclaimer, the term of this patent is extended or adjusted under 35 U.S.C. 154(b) by 0 days.

(21) Appl. No.: 10/295,608

(22) Filed: Nov. 15, 2002

(51) Int. Cl.[7] .................................................. A61F 13/00
(52) U.S. Cl. .................................... 5/650; 5/621; 5/624
(58) Field of Search .......................... 5/650, 646, 648, 5/621, 624; 128/845, 846

(56) References Cited

U.S. PATENT DOCUMENTS

| | | | | |
|---|---|---|---|---|
| 3,532,336 A | * | 10/1970 | Baker | 5/650 |
| 4,910,818 A | * | 3/1990 | Grabill et al. | 5/650 |

* cited by examiner

Primary Examiner—Teri Pham Luu
Assistant Examiner—Fredrick Conley
(74) Attorney, Agent, or Firm—Porter Wright Morris & Arthur, LLP

(57) ABSTRACT

A device for positioning a patient for medical imaging comprising an inclined surface comprising a radiotranslucent low end segment and a high end segment. The inclined surface comprises a concave-shaped recess for supporting the patient's torso at the low end segment and legs at the high end. The low end and high end of the inclined surface form an obtuse angle with respect to each other. The device also comprises at least one inclined surface support that may be attached to the inclined surface at the low end or, alternatively, to the high end. The support supports the inclined surface such that the high end has a height greater than the low end.

20 Claims, 5 Drawing Sheets

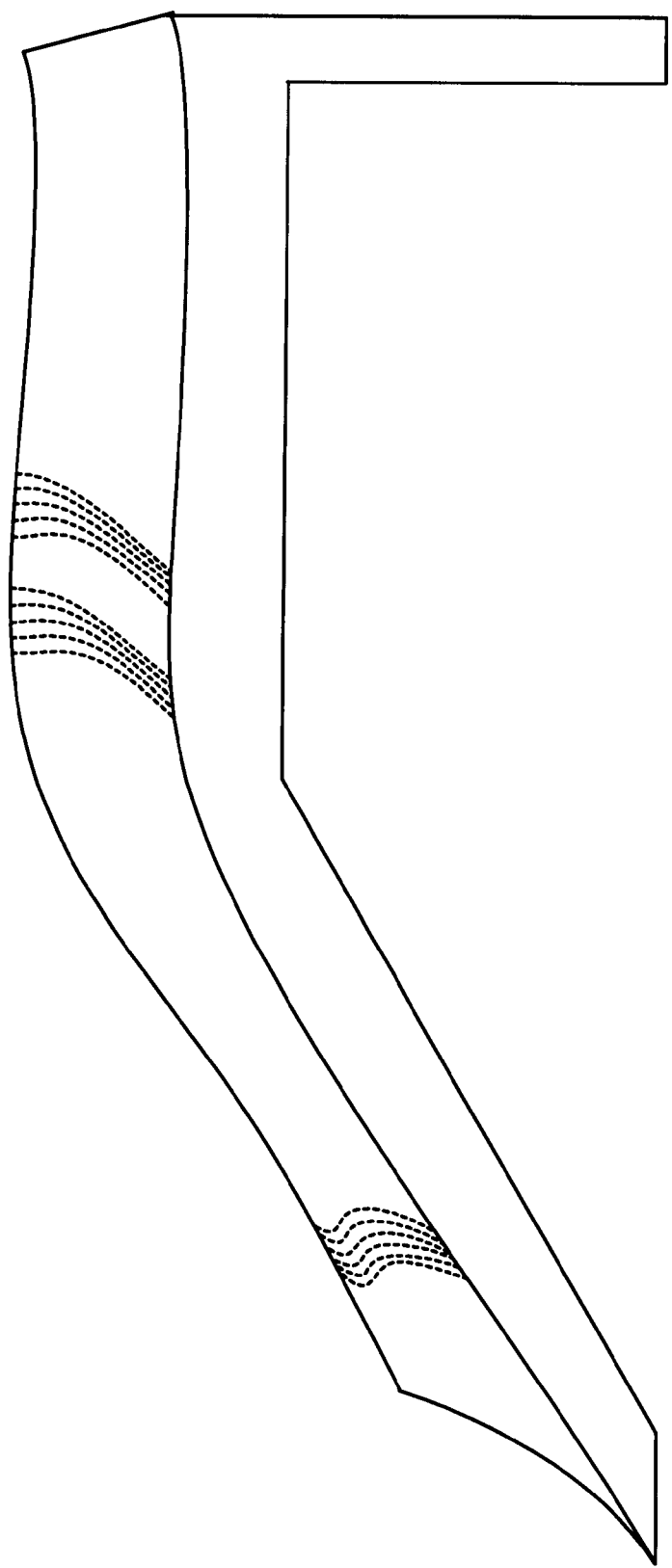

BODY POSITIONER

BACKGROUND

Medical imaging techniques, such as x-ray, magnetic resonance imaging (MRI), computed tomography (CT), fluoroscopy, ultrasound, and the like are performed to analyze the internal structures of various parts of the body. Images of the head are used to diagnose traumatic injuries, such as blood clots or skull fractures, tumors, and infections. Images of the spine, which reveal the bony structure of the vertebrae as well as the intervertebral discs and spinal cord, are used to assist in the diagnosis of a wide range of injuries and diseases, such as fractures, fusion of joints, arthritis, localization of a foreign body, determination of chronic pain, osteoporosis and the like.

Body positioning is important in obtaining specific planar views in imaging the head and spine. Correct positioning of the spine provides an overall impression of the spine and may show tumors and other pathological processes. Imaging is used to demonstrate the range of movement of the spine, the intervertebral foramen, facet joints, and disc sizes and shape. Imaging of the whole of the spine is used in the detection and measurement of scoliosis. The head and spine may be imaged in any plane to provide detailed information of soft tissue and bone detail, effective in the diagnosis of disc herniation, facet joint disease, osteoarthritis, disc bulges, and nerve root entrapment.

Imaging of certain spinal defects, such as curvatures of the spine, is difficult due to the patient aperture space available in many imaging devices. An example of this problem is seen in the kyphotic patient. Kyphosis is forward curvature of the spine caused by a deformity affecting the vertebrae. Destruction of the vertebral bodies as a result of diseases such as osteoporosis produces collapse of vertebral bodies and the characteristic appearance known as Dowager's hump. A patient presenting with severe kyphosis is unable straighten his neck to a normal position when lying on his back. To obtain proper images of the spine or head, the body of a patient with a spinal defect, such as kyphosis, must be elevated. Currently, pillows or cushions are used so that the head may be positioned inside the patient aperture of a medical imager.

Medical imaging of the head or spine currently requires that a patient remain motionless in a specific position during the imaging for up to an hour. Maintaining a given position without moving for that length of time proves difficult for many patients. The pillows used to prop the patient may slip, produce inconsistent results, or cause discomfort to the patient. Accordingly, a need exists for improved medical imaging positioning devices and methods.

SUMMARY

A device for positioning a patient for medical imaging comprising an inclined surface comprising a radiotranslucent low end segment and a high end segment. The inclined surface further comprises a concave-shaped recess for receiving the patient's torso at the low end segment and legs at the high end. The low end and high end of the inclined surface form an obtuse angle with respect to each other. The device further comprises at least one inclined surface support that may be attached to the inclined surface at the low end or alternatively, to the high end. The support supports the inclined surface such that the high end has a height greater than the low end.

BRIEF DESCRIPTION OF THE DRAWINGS

FIG. 4 is a perspective side view showing an additional embodiment of the invention.

DESCRIPTION

Figure 1:
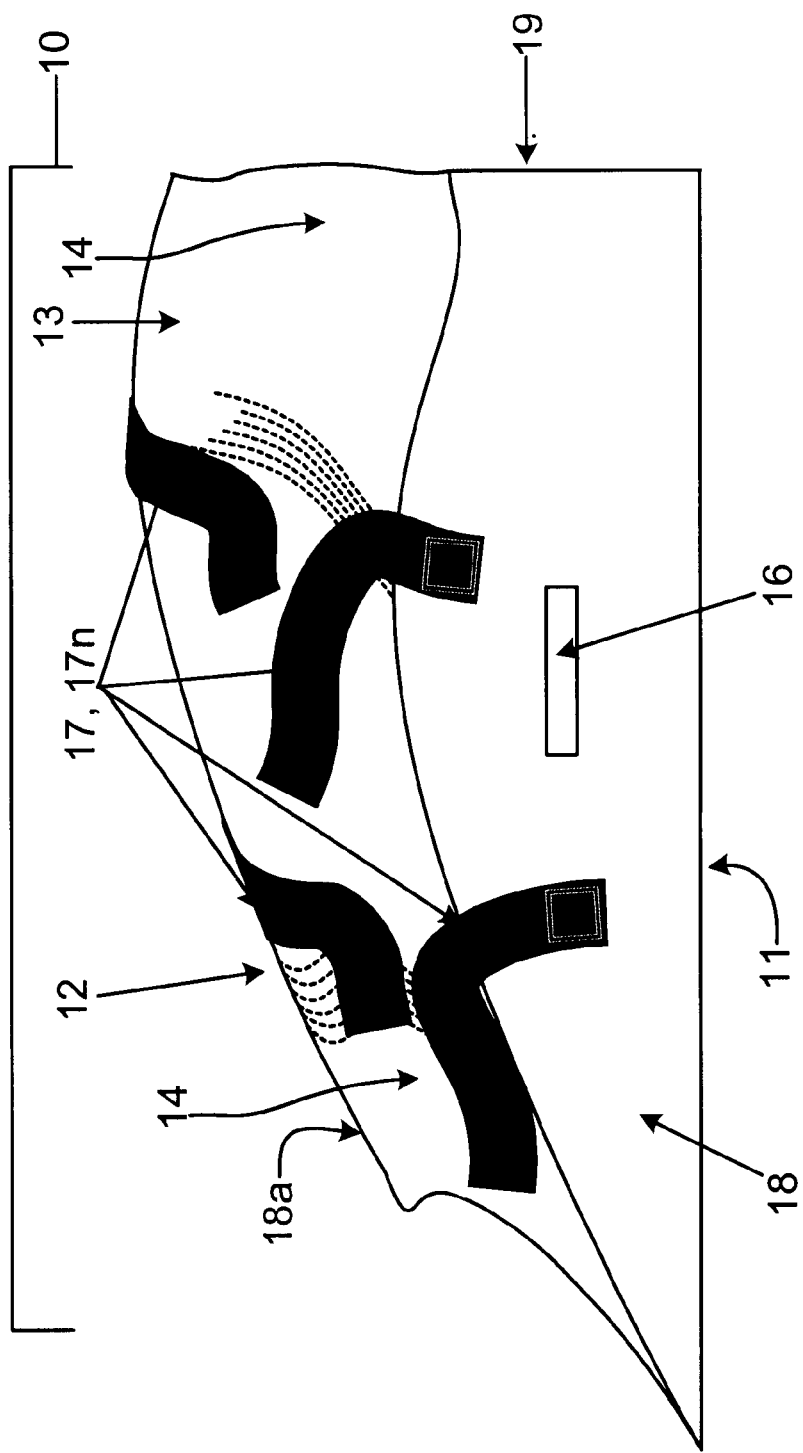
FIG. 1 is a perspective side view showing an embodiment of the invention with optional restraints.

A body positioner used in medical imaging of the head and/or spine is disclosed. As shown in the Figures, the device comprises an inclined surface 10 and at least one inclined surface support 11. The device comprises any material, such as plastic, a textile, and the like or a combination of materials. The device is of sufficient thickness to provide support, yet sufficiently thin to remain relatively lightweight. The entire device or the inclined surface 10 portion may be covered and/or padded. The covering and padding may comprise the entire device or inclined surface or portions of each, and may be removable.

The inclined surface 10 extends from a low end segment 12 to a high end segment 13. The high end 13 has a height greater than that of the low end 12. The low end 12 and the high end 13 are angulated with respect to each other in an obtuse angle relationship. In an embodiment, the low end segment 12 intersects with the high end segment 13 at an angle of about 135°. The inclined surface may comprise additional segments, and may alternately comprise a curvilinear shape.

The width and height of at least a portion of the low end segment 12 is made from a radiotranslucent material and made to fit within the inner diameter of a patient aperture of a medical imager, such as, but not limited to, CT, MRI, x-ray, fluoroscopy and ultrasound devices. The length of the inclined surface 10 accommodates pediatric to adult patients.

Figure 2:
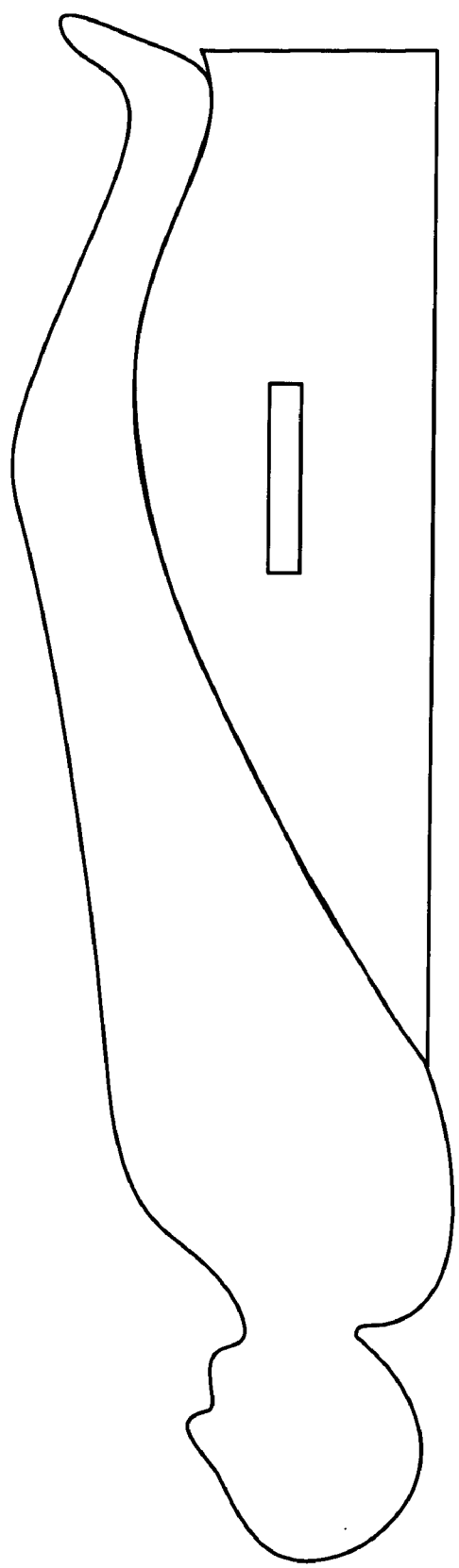
FIG. 2 is a side view of a patient with kyphosis positioned on an embodiment of the invention.

As shown in the Figures, the inclined surface 10 further comprises a generally concave-shaped recess 14 extending generally the length of the inclined surface 10. The recess 14 is shaped to support a portion of the body of a patient in a supine position. As illustrated in FIG. 2, the device supports at least a part of the torso and the legs of a patient. The recess 14 may be uniform, or may be shaped to follow the contour of a human shape. The recess 14 at the low end 12 may comprise inclines and depressions or other similar features shaped to accommodate the patient's back at the point of contact. The recess 14 at the high end 13 may comprise a single depression shaped to accommodate both legs together or individual depressions that accommodate each leg individually.

Figure 3:
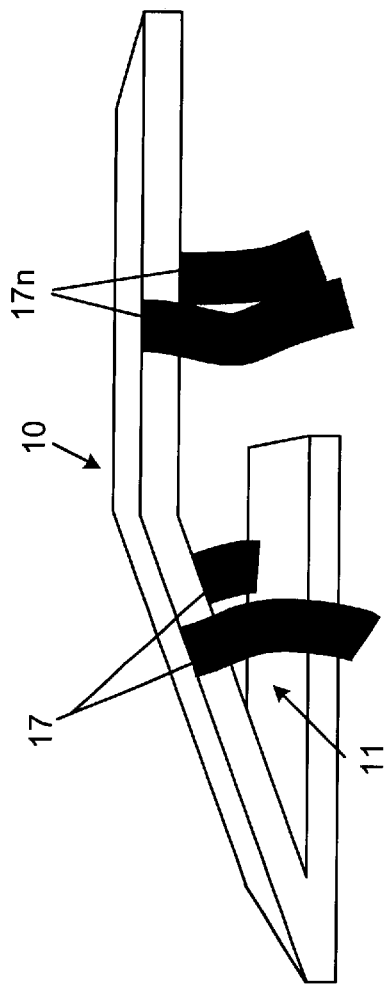
FIG. 3 is a perspective side view showing another embodiment of the invention with an alternative placement of a restraint.

The inclined surface support 11 may be attached to the inclined surface 10 at an edge of the low end 12 or, alternatively, at an edge of the high end 13. FIG. 3 shows an inclined surface support 11 intersecting with the low end 12. In this embodiment, the support 11 extends in a generally horizontal plane from the low end 12. In an alternative of this embodiment, the support 11 extends to a point sufficient for the support 11 to firmly support the inclined surface 10 without motion. The area defined between the inclined surface 10 and the support 11 may comprise one or more brace 30 or may be a solid. This embodiment is fabricated from a relatively rigid plastic. The device may further comprise a pad and/or a covering, which may be attached or removable.

Figure 1A:
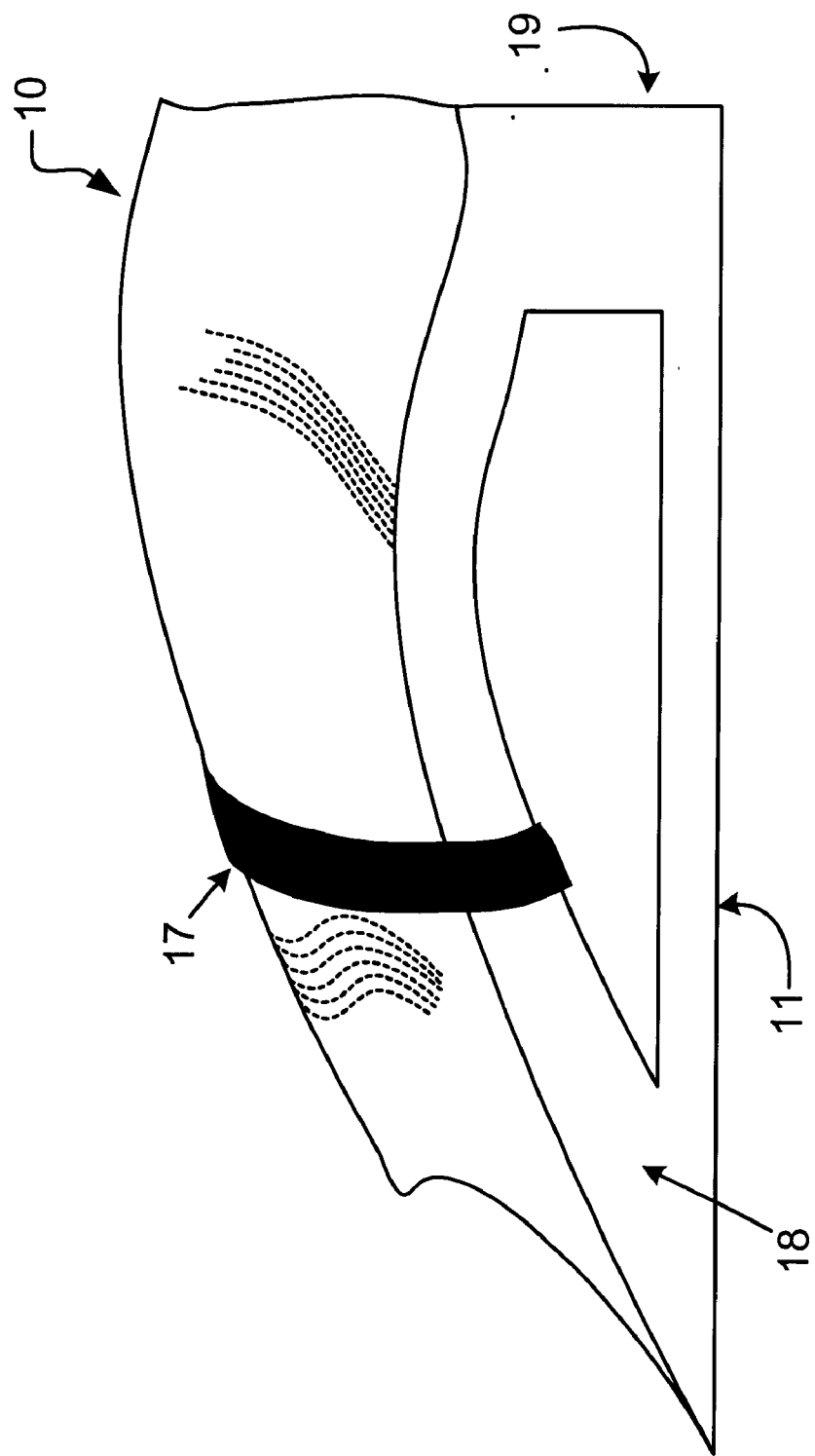
FIG. 1A is an alternate embodiment of the invention.

As shown in FIG. 1, the inclined surface support 11 may alternatively extend the length of the inclined surface 10 to form a solid shape. In this embodiment, the device further comprises sidewalls 18, 18a and an end 19. In a variation of this embodiment, the device comprises a hollow shape, such as illustrated in FIG. 1A. Either shape may comprise a foam rubber; however, anything, such as plastic, textile, air, or the like may be used. The shape may further comprise padding and/or a covering, which may be attached or removable.

FIG. 4 illustrates an additional embodiment with the inclined surface support 11 extending from an edge of the high end 13. In this embodiment, the support 11 extends vertically from the high end 13 to a plane essentially equal to that of an edge of the low end 12. This embodiment is fabricated from a relatively rigid plastic. The device may further comprise a pad and/or a covering, which may be attached or removable.

As shown in FIG. 1, the device may include at least one restraint 17, 17n to assist in holding a patient against the inclined surface 10. The restraint 17, 17n may be any mechanism to hold a portion of the patient's body, such as the torso and/or legs. Examples of restraints include mechanisms that a patient slips through, such as an attached piece with elastic banding, and mechanisms that secure the patient after the patient is placed on the inclined surface 10, such ties, stretchable or non stretchable components that join, and the like. More than one restraint may be used in combination.

In an embodiment, the restraint 17 comprises a hook and loop fastener of sufficient length to interlock snugly over a portion of the patient's body, such as the torso and/or legs, and of sufficient width to hold the patient firmly against the inclined surface 10. In an embodiment, the device comprises a first hook and loop fastener that holds the patient's torso and a second hook and loop fastener that holds the patient's legs.

Figure 3A:
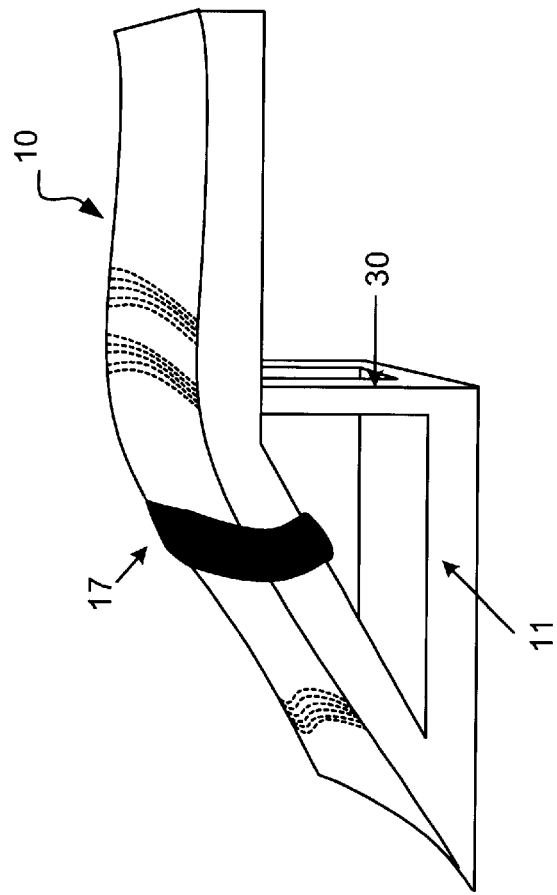
FIG. 3A shows an additional embodiment with an alternative restraint.

The restraint 17, 17n may be attached to any surface or, alternatively, to a cover. As shown in FIG. 1, the restraint 17, 17n may be attached to opposing sidewalls. The restraint 17, 17n may be attached to the inclined surface 10 as shown in FIG. 3, or attached to a bottom of the inclined surface 10 as shown in FIG. 3A. The restraint 17, 17n may also extend through the hollow portion of the shape, as illustrated in FIG. 1A. Those skilled in the art will appreciate other numbers, combinations and placement of restraints given the present disclosure.

The device may further comprise one or more strap 16 to assist in moving the shape. The strap 16 may be located on any surface and may alternately be located on a cover.

The device allows manipulation of the head and/or spine for medical imaging. As illustrated in FIG. 2, the device allows a patient with a spinal deformity, such as kyphosis, to be positioned within the patient aperture of an imaging device for imaging the head and/or spine. The device also allows for proper body positioning to image the head and/or spine of patients with other spinal deformities. Alternatively, the device may be used for patients without spinal deformities. An example of alternative uses would be to obtain images of the vertebrae where the thoracic vertebrae are in a straightened configuration, rather than in their normal curved array.

While the invention is described in some detail with specific reference to certain embodiments and alternatives, there is no intent to limit the invention disclosed to a particular embodiment or specific alternatives. Therefore, the true scope of the invention is defined not by the foregoing description but by the following claims.

What is claimed is:

1. A device for positioning a patient for medical imaging comprising:

an inclined surface, said surface comprising a radiotranslucent low end segment and a high end segment, said inclined surface comprising a concave-shaped recess to receive the patient's torso at the low end segment and legs at the high end, said concave-shaped recess supporting the torso such that an upper portion of the torso is positioned lower than a lower portion of the torso to allow medical imaging of the patient's head and/or spine, said low end and high end forming an obtuse angle with respect to each other; and at least one inclined surface support, said support attached to the inclined surface at either the low end or the high end, said support supporting the inclined surface such that the high end has a height greater than the low end.

2. The device of claim 1 wherein the obtuse angle is about 135°.

3. The device of claim 1 wherein the inclined surface has a dorsal surface that is curvilinear.

4. The device of claim 1 further comprising a brace.

5. The device of claim 1 wherein the low end segment has a width capable of fitting within an inner diameter of a patient aperture of a medical imager.

6. The device of claim 1 wherein the inclined surface and the support comprise a relatively rigid material.

7. The device of claim 1 further comprising a pad.

8. The device of claim 1 further comprising at least one restraint.

9. The device of claim 8 wherein the restraint is a band, a stretchable band, at least one tie, a joinable stretchable component, or a joinable nonstretchable component.

10. The device of claim 8 wherein the restraint is a hook and loop fastener, said fastener positioned to secure at least a portion of the patient's body to the inclined surface.

11. The device of claim 10 wherein the fastener secures at least one of the patient's torso and the patient's legs.

12. The device of claim 1 wherein the recess is shaped to conform to the patient's back, buttocks and legs.

13. The device of claim 1 further comprising a strap to assist in moving the device.

14. The device of claim 1 wherein the inclined surface support extends from the low end, said device further comprising:

two opposing sidewalls extending from each opposite lateral side of the inclined surface; and an end extending from an edge of the high end segment, said end connected to an edge of each sidewall and the inclined surface support such that the inclined surface, inclined surface support, sidewalls and end form a solid shape.

15. The device of claim 14 wherein the solid shape further comprises a hollow portion.

16. The device of claim 15 further comprising at least one restraint.

17. The device of claim 16 wherein the restraint is a hook and loop fastener, said fastener positioned to secure at least a portion of the patient's body to the inclined surface.

18. The device of claim 17 wherein the fastener secures at least one of the patient's torso and the patient's legs.

19. A device for positioning a patient for medical imaging comprising:

an inclined surface, said surface comprising a radiotranslucent low end segment and a high end segment, said inclined surface comprising a concave-shaped recess for receiving the patient's torso at the low end segment and legs at the high end, said concave-shaped recess supporting the torso such that an upper portion of the torso is positioned lower than a lower portion of the torso to allow medical imaging of the patient's head and/or spine, said low end and high end forming an obtuse angle with respect to each other;

an inclined surface support, said support attached to the inclined surface at the low end;

at least two opposing sidewalls extending from each lateral side of the inclined surface, said sidewalls comprising a strap and at least one hook and loop fastener for holding the patient against the inclined surface; and an end extending from an edge of the high end segment, said end connected to an edge of each sidewall and the inclined surface support.

20. A device for positioning a patient for medical imaging comprising:

an inclined surface, said surface comprising a radiotranslucent low end segment and a high end segment, said inclined surface comprising a concave-shaped recess for receiving the patient's torso at the low end segment and legs at the high end, said concave-shaped recess supporting the torso such that an upper portion of the torso is positioned lower than a lower portion of the torso to allow medical imaging of the patient's head and/or spine, said low end and high end forming an obtuse angle with respect to each other;

an inclined surface support, said support attached to the inclined surface at either the low end or the high end; and at least one hook and loop fastener for holding the patient against the inclined surface.

* * * * *